United States Patent [19]

Vit

[11] 4,012,842
[45] Mar. 22, 1977

[54] DENTAL TREATMENT METHOD AND APPARATUS

[75] Inventor: Jaroslav Vit, Belle Mead, N.J.

[73] Assignee: National Patent Development Corporation, New York, N.Y.

[22] Filed: Nov. 19, 1974

[21] Appl. No.: 525,258

Related U.S. Application Data

[63] Continuation-in-part of Ser. No, 312,507, Dec. 6, 1972, Pat. No. 3,863,628, which is a continuation-in-part of Ser. No. 301,071, Oct. 26, 1972, abandoned, which is a continuation-in-part of Ser. No. 301,074, Oct. 26, 1972, abandoned.

[30] Foreign Application Priority Data

| June 12, 1972 | United Kingdom | 27445/72 |
| Aug. 24, 1972 | United Kingdom | 39588/72 |
| Aug. 24, 1972 | United Kingdom | 39589/72 |
| Aug. 24, 1972 | United Kingdom | 39590/72 |
| Sept. 5, 1972 | United Kingdom | 41194/72 |

[52] U.S. Cl. .......................... 32/58; 128/66; 424/53

[51] Int. Cl.² .................. A61H 09/00; A61K 07/16

[58] Field of Search ............... 32/58; 128/66, 62 A

[56] References Cited

UNITED STATES PATENTS

| 2,759,266 | 8/1956 | Cassani | 32/58 |
| 3,420,228 | 1/1969 | Kalbfeld | 128/66 |
| 3,522,801 | 8/1970 | Robinson | 128/66 |
| 3,547,110 | 12/1970 | Balamuth | 128/66 |
| 3,636,947 | 1/1912 | Balamuth | 128/66 |
| 3,886,266 | 5/1975 | Goldman et al. | 424/53 |

FOREIGN PATENTS OR APPLICATIONS

1,916,507   10/1969   Germany ............... 32/DIG. 4

*Primary Examiner*—John F. Pitrelli
*Attorney, Agent, or Firm*—Cushman, Darby & Cushman

[57] ABSTRACT

In a method for removal of dental plaque and caries in dentistry, there is applied to the teeth a high velocity pulsating jet stream of liquid possibly subjected also to ultrasonic vibration. The jet stream is pulsated, preferably with pulsations having a pressure-time wave form which includes, in each cycle, a period of lowered pressure or nil pressure sufficient for relaxation of the attacked material leading to mechanical fatiguing. The liquid may be neutral to the attacked material for a plaque removal, e.g., water, but for carie removal has a chemical action provided by an alkaline solution containing N-chloro and/or N-dichloro compounds resulting from interaction of certain hypohalites and amine compounds capable of removing plaque and caries both. The method is effective without the application of ultra-sonic vibrations, although their utilization with the aforesaid mechanical fatiguing pulsations is most effective. Utilization of ultra-sonic vibrations with harmonic pulsations is also effective. An embodiment of apparatus for application of the pulsating jet stream in dentistry incorporates pump means designed for providing the preferred pulsation wave forms. Preferably, the pump means is driven by a rotary cam co-acting with a cam follower which is adjustable to vary the duration of the pressure stroke during each cycle.

11 Claims, 17 Drawing Figures

DENTAL TREATMENT METHOD AND APPARATUS

This application is a continuation-in-part of my copending U.S application Ser. No. 312,507, filed Dec. 6, 1972 now U.S. Pat. No. 3,863,628 entitled DENTAL DEVICE which in turn is a continuation-in-part of my copending application Ser. No. 301,071 filed Oct. 26, 1972 and abandoned, entitled DENTAL PLAQUE REMOVAL, and my copending application Ser. No. 301,074, filed Oct. 26, 1972 and now abandoned, entitled JET STREAM.

This invention relates to dentistry and more particularly to an improved method of removing tooth caries and plaque.

In my copending application Ser. No. 301,163, filed Oct. 26, 1972 entitled DENTAL TREATMENT, there is disclosed a dental treatment for removing caries and preparing teeth for filling in which the teeth are brought into contact with an N-haloamine solution without the necessity of using drills or like. The treatment is also disclosed as being useful in removing plaque.

The present invention is concerned with improvements in the application of the aforesaid solutions to the teeth whereby a much more rapid and effective carie removal can be accomplished through a combined mechanical and chemical action.

One of the disclosed methods of applying the chemical solutions recited in the aforesaid application is by the use of a WATER PIC ™ device, see U.S. Pat. No. 3,227,158. These devices are known in the art for use in oral hygiene — cleaning of teeth, massaging gums and for plaque removing. A device of this type embodies structure operable to deliver a water jet stream pulsating at 800 to 1600 cycles per minute at maximum pressure 90 pounds per square inch through a jet orifice of 0.025 to 0.045 inches in diameter.

While the present invention is particularly concerned with the improvements in delivering an aqueous solution as herein contemplated to teeth for carie and plaque removal, the invention may likewise be viewed as an improvement in the aforesaid method and apparatus for applying water to the teeth for oral hygienic purposes such as plaque removing, teeth cleaning and gum massaging.

In accordance with the principles of the present invention a significant improvement in obtaining a rapid and effective debris removal from teeth is obtained by modifying the above-mentioned pulsating jet stream so that in each pulse cycle the difference between the highest pressure and a lowered pressure applied to the material and the respective periods for which the material is under highest pressure and lowered pressure causes the material to be mechanically stressed and then completely relaxes so as to establish an erosion by fatique which materially enhances caries removal.

Accordingly, it is an object of the present invention to provide an improved method of applying the aforesaid chemical solutions to teeth for the purposes of complete caries removal in preparing teeth for filling without the use of drills, as well as for purposes of plaque removal, which embodies the principles enunciated above.

Another object of the present invention is the provision of a method of establishing an improved pulsating water jet stream of the type described for use in oral hygiene including teeth cleaning, gum massaging and plaque removing.

Another object of the present invention is the provision of an improved apparatus for caries removal in preparing teeth for filling which eliminates or minimizes the need for drills and the like and operates in accordance with the principles enunciated above; mechanical means such as drills are necessary for the undercutting or opening of the cavity only.

Another object of the present invention is the provision of an improved apparatus of the type described operable to remove plaque from teeth.

In accordance with the principles of the present invention, it has been found that caries and plaque removal can be further facilitated by the application of untra-sonic vibration to the pulsating jet stream both when used with the aforesaid chemical solution to supplement the chemical action thereof as well as the oral hygienic action of a pulsating water jet stream.

Accordingly, it is a further object of the present invention to provide an improved method of caries and plaque removal embodying the application of ultra-sonic vibrations to a pulsating jet stream.

Another object of the present invention is the provision of an improved apparatus of the type described having means for imparting ultra-sonic vibrations to the pulsating jet nozzle so as to both enhance the material removing effect of the pulsating liquid jet stream and the material removing capability of the nozzle itself when brought into contact with the material to be removed during operation.

These and other objects of the present invention will become more apparent during the course of the following detailed description and appended claims.

The invention may best be understood with reference to the accompanying drawings wherein an illustrative embodiment is shown.

It is known to utilize a pulsating high velocity jet stream of liquid as a means for cleaning of the mouth. It has not hitherto been possible to effect complete removal of caries. It was found and it is an object of this invention, that caries can be removed and teeth prepared for filling if a solution of N-haloamine acid at an alkaline pH usually 8 to 12, e.g., between 10.5 and 11.5, is delivered on a carious area as a pulsating liquid jet stream; the same can be used for plaque removal, however, the chemical action is only improving the effect while for removal of caries chemical effect is necessary.

In accordance with the invention it has been found that the shape of the time-pressure relationship curve of the jet stream pulsations is a very important factor, much more so than frequency and pressure. By selection of a suitable time-pressure curve, there is introduced a period for complete relaxation of the attacked material, between each pulse.

Figure 1:
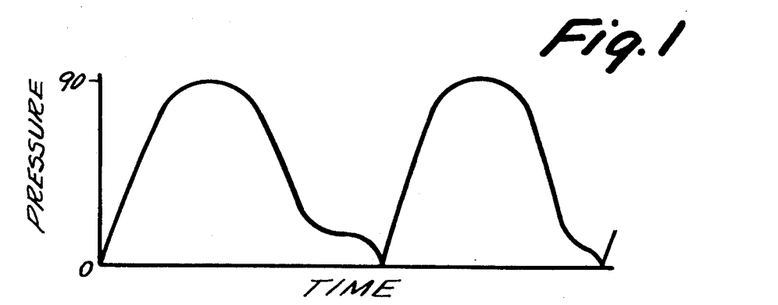
FIGS. 1 and 2 are graphs to show the time-pressure relationship of pulsed liquid streams used currently in the art.
Figure 2:
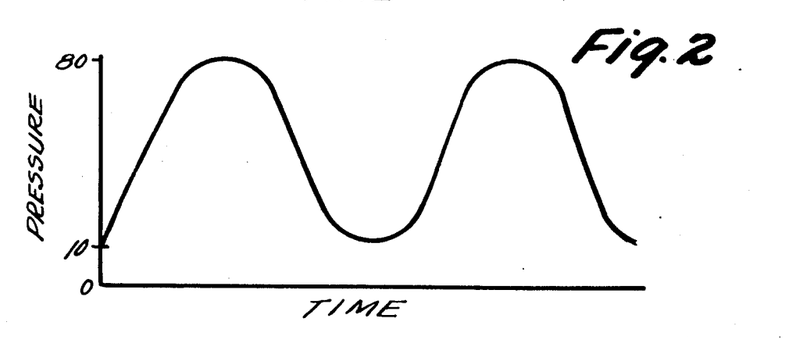
Figure 3:
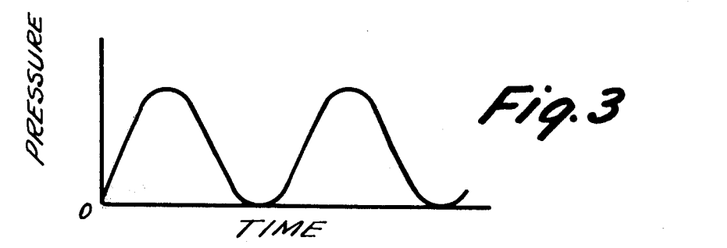
FIGS. 3 to 6 are graphs to show the time-pressure relationship of certain pulsed liquid streams which were investigated during the making of the present invention.
Figure 4:
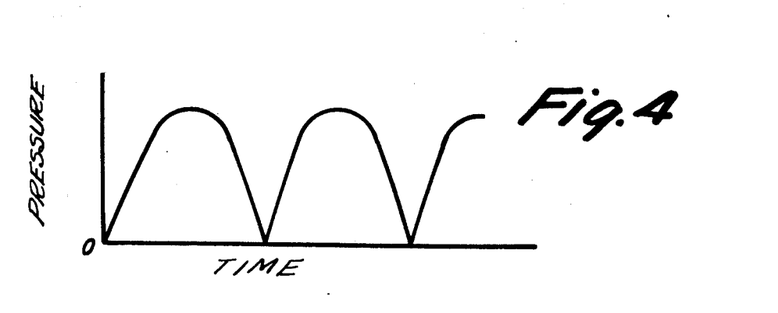
Figure 5:
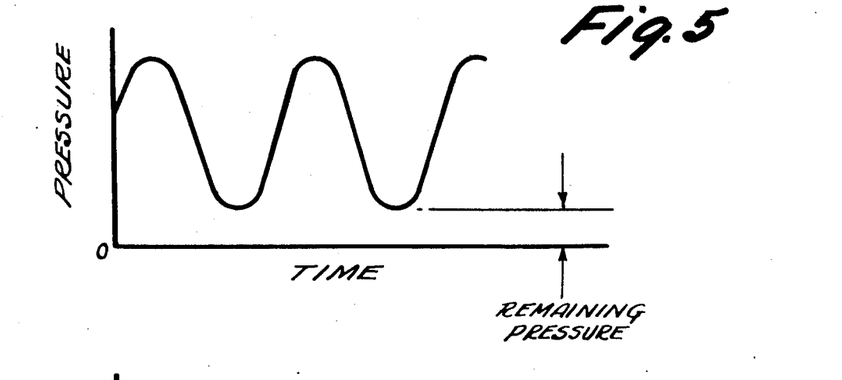
Figure 6:
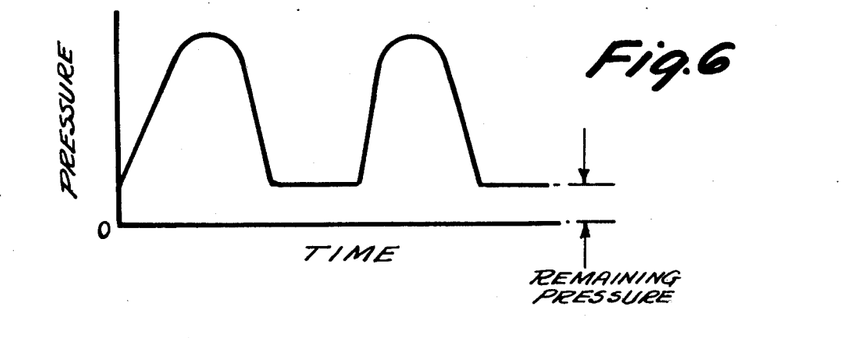
Figure 7:
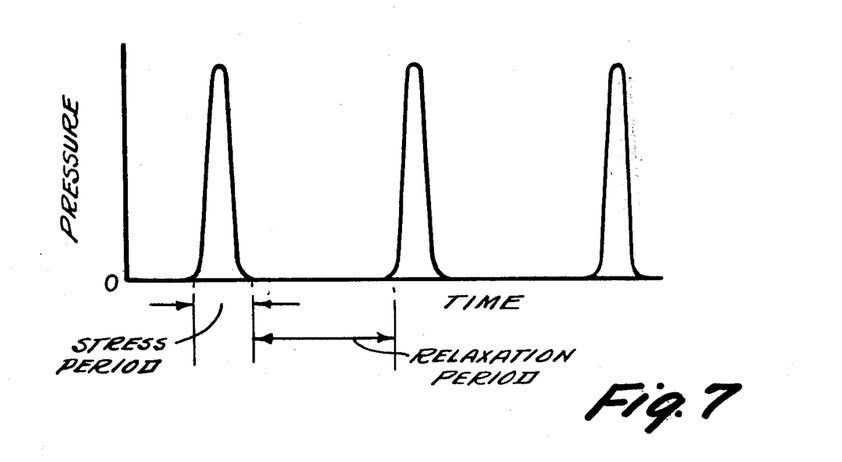
FIGS. 7 and 8 are graphs showing the time-pressure relationship of pulsed liquid streams in accordance with this invention.
Figure 8:
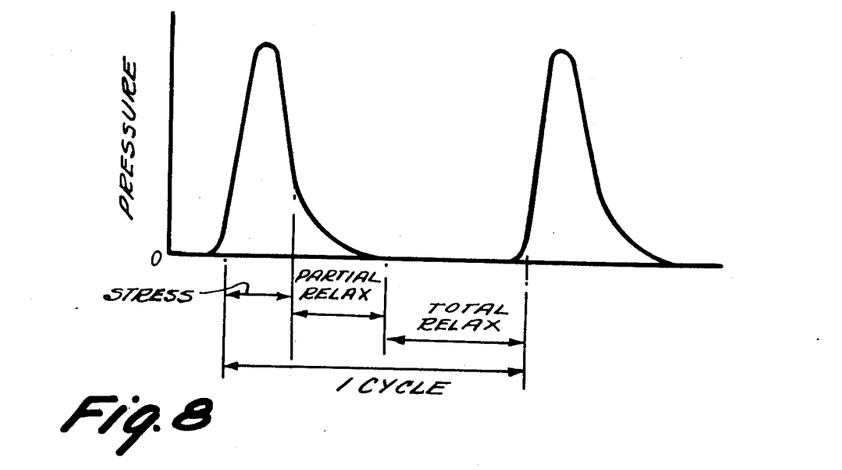

In the accompanying drawings, FIGS. 1 and 2 show the time-pressure curve of the prior art method and apparatus, whereas FIGS. 3 to 6 show other such curves which are obtainable. FIGS. 7 and 8, in contrast, show curves in which there is zero application of pressure to the material for a prolonged period between each pulsation.

Figure 9:
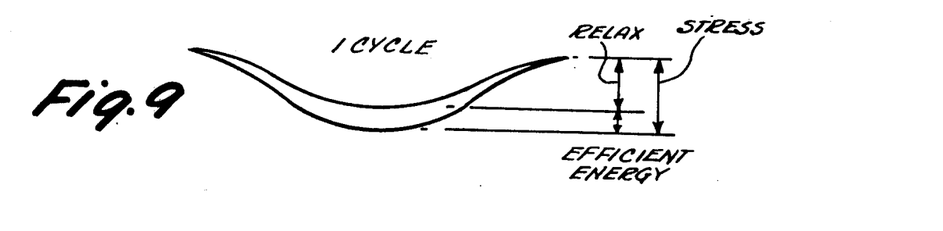
FIG. 9 is a diagrammatic representation of a fiber to show its reaction to being stressed by a pulsed liquid stream in accordance with FIGS. 1 to 6.
Figure 10:
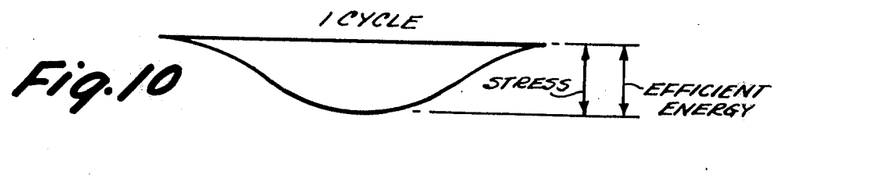
FIGS. 10 and 11 are diagrammatic representations of a fiber to show its reaction to being pressed respectively by the pulsed liquid streams in accordance with FIGS. 7 and 8.
Figure 11:
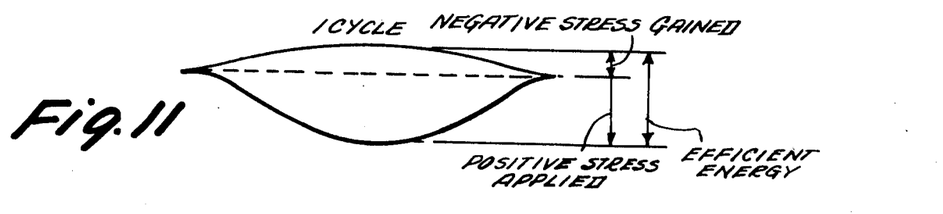

The pulsating jet streams represented by FIGS. 3, 4, 5 and 6 are far less efficient than the streams represented by FIGS. 7 and 8, and the best results are obtained with the stream shown on FIG. 7. While all the pulsating jet streams represented by FIGS. 1 to 6 cause stress changes in the material being treated, they do not allow for its relaxation, not even the streams represented by FIGS. 1, 3 and 4, wherein the pressure keeps dropping to zero with each cycle, because the time allowed at zero pressure is infinitesimal. Complete relaxation of the material requires a certain period of time, according to its elasticity. On the other hand, the time element involved in a period of applying of stress is incomparably shorter. As a means of showing changes of shape of a stressed material under applied pressure, an elastic fiber can be used. Pulsating liquid jet streams represented by FIGS. 1 to 6 will cause vibrations, of a fiber in the manner shown in FIG. 9, whereas jet streams represented by FIG. 7 or 8 will allow, due to the presence of a proper relaxation period, much larger vibrations, as shown in FIGS. 10 and 11. A similar phenomenon occurs of solid elastic material such as dental plaque or caries. These materials are therefore efficiently eroded in depth, fatiquing in a relatively short period of time (seconds for plaque, minutes for caries), and therefore these materials can be removed by erosion, rather than by hydrodynamic abrasion. Since the elastic properties of dental materials differ from case to case, it is desirable to provide flexible equipment, allowing for adjustment to the most efficient frequencies and pressures, both independently. The existing devices do not allow for independent adjustment of frequencies and pressures, nor do they allow for adjustment of the time element allowed for stress and relaxation within a cycle.

Figure 12:
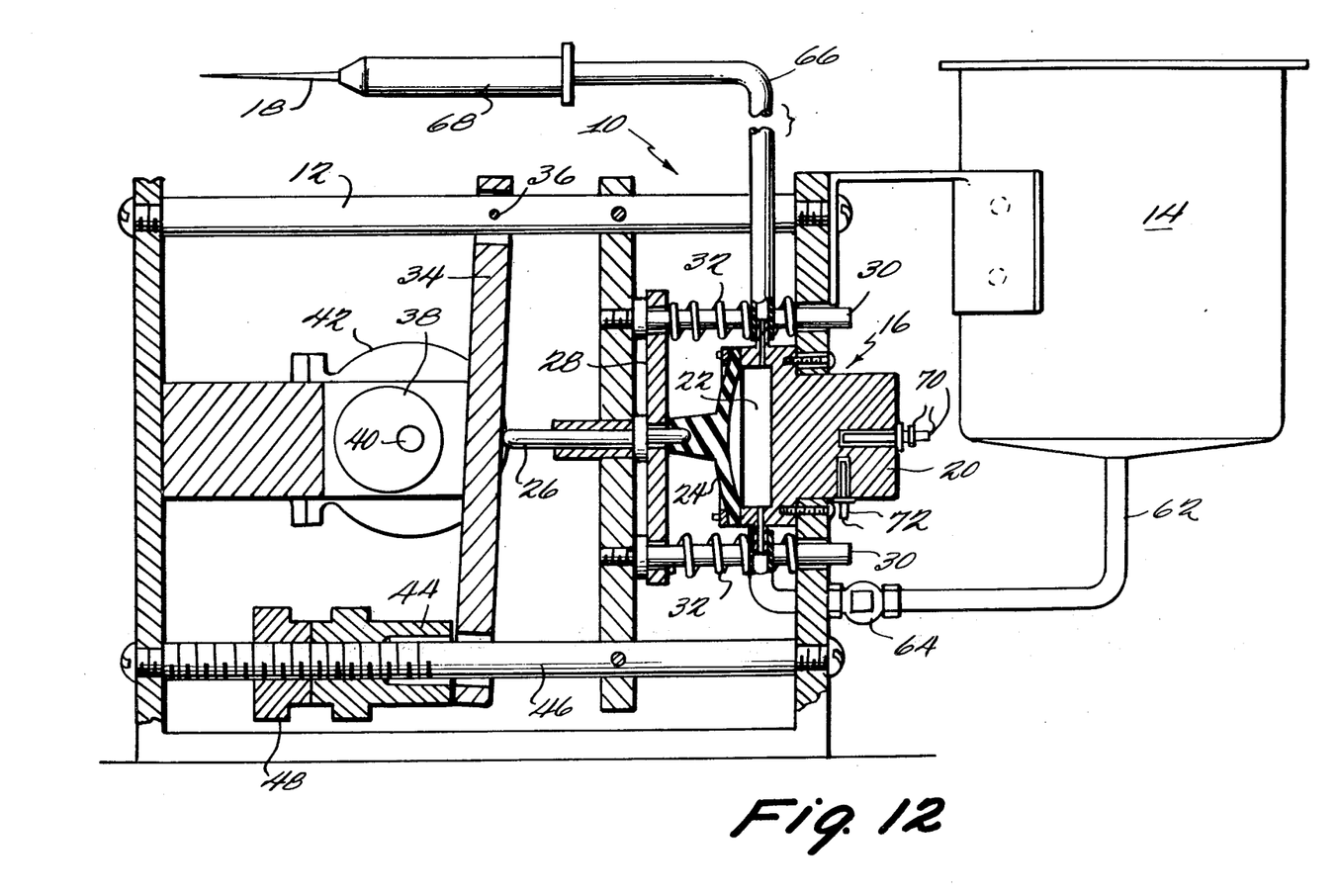
FIG. 12 is a side elevational view of a variable flow pump mechanism for producing pulsed liquid streams in accordance with FIGS. 7 and 8.

Referring now more particularly to FIG. 12, there is shown therein a device, generally indicated at 10, for producing a pulsed liquid jet stream, with time and pressure variable to permit the formation of the characteristic curves of FIGS. 7 and 8. As shown, the device 10 includes a fixed frame structure 12, which may be of any conventional construction, suitably configured to support a container or receptacle 14 for the liquid supply and a power driven pump mechanism, generally indicated at 16, for delivering the supply of liquid contained within the receptable 14 to a discharge nozzle 18 which, as shown, is in the form of a hypodermic needle.

The pump mechanism 16, as shown, is preferably of the flexible diaphragm type, although it will be understood that piston and cylinder types as well as flexible bellows types may be utilized if desired. As shown, the pump mechanism includes a pump body 20 of a suitable heat conductive material, such as metal or the like, defining an open ended pump chamber 22 disposed with its axis extending generally horizontally. The open end of the pump chamber 22 is closed by flexible diaphragm 24, formed of any suitable resilient or flexible material such as rubber, plastic or the like.

Embedded within the central portion of the diaphragm 24 and extending axially outwardly therefrom is a plunger rod 26. Fixedly connected to the rod 26 at a position adjacent the diaphragm 24 is the central portion of a cross-head plate 28. The ends of the plate 28 are apertured to guidingly receive therein a pair of guide rods 30 suitably fixed to the frame structure 12 in parallel relation to the plunger rod 26. The plunger rod 26 and diaphragm is resiliently urged into an outward limiting position, as shown, by suitable spring means such as a pair of coil springs, 32, disposed in surrounding relation to the guide rods with the ends thereof abutting the cross-head plate 28 and frame 12 respectively.

Movement of the plunger rod 26 and diaphragm 24 away from and toward the limiting position in successive cycles of operation is accomplished preferably by a cam and cam follower assembly which, as shown, includes a cam follower arm 34 pivoted at one end to the frame structure 12, as indicated at 36, and having its central portion disposed in abutting engagement with the outer end of the plunger rod 26. In lieu of the cam and cam follower assembly, one can use other means, e.g., solenoid. Disposed on the side of the central portion of the cam follower arm opposite the plunger 26 is a cam 38 fixed to a shaft 40 drivingly connected to the output shaft of a variable speed electric motor 42 suitably supported on the frame structure 12. The end of the cam follower arm 34 opposite from the pivot 36 is disposed in a position to abut an adjustment member 44 suitably threaded on an elongated member 46 which is either fixed to the frame structure or forms a part thereof. A lock nut 48 is also threaded on the member 46 to retain the adjusting member in any desired position of adjustment along the member 46.

Figure 13:
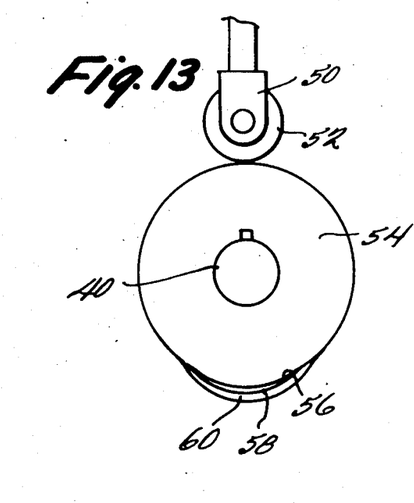
FIG. 13 is a fragmentary end view of a modified form of cam and cam follower arrangement.
Figure 14:
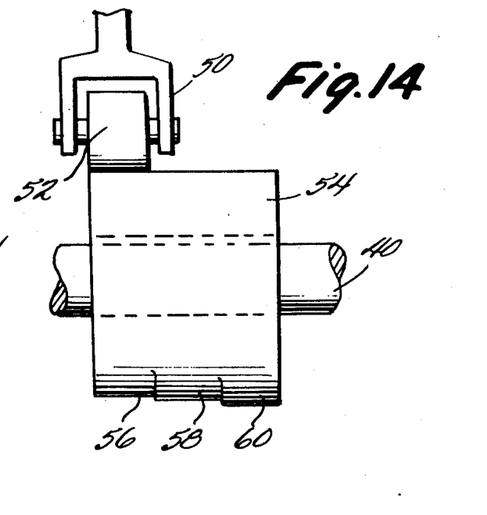
FIG. 14 is a fragmentary front elevational view of a cam and cam follower arrangement shown in FIG. 13.

FIGS. 13 and 14 illustrate another cam and cam follower arrangement which could be utilized in lieu of the arrangement described above. As shown in FIGS. 13 and 14, the end of the plunger rod 26 is bifurcated, as indicated at 50, and has a cam follower roller 52 journaled therebetween. A cam 54 is keyed to the shaft 40 in such a way as to be movable axially with respect to the shaft. The cam 54 is constructed with different axially spaced continuous contact cam surfaces 56, 58 and 60, any one of which can be brought into contact with the cam follower roller 52 by adjusting the axial position of the cam 54 on the shaft 40. Such a continuous contact cam drive has a lower noise level and may be made more durable than the intermittent drive of FIG. 12.

It will be understood that both of the above arrangements provide the operator with the capability of adjusting the dwell time of each cycle. A fixed performance device, however, may be desirable from the standpoint of economics and is thus contemplated by the present invention in its broadest aspects.

In order to enable the cycling of the pump mechanism 16 to deliver the supply of liquid in container 14 through the nozzle 18 as a pulsating jet stream, an inlet tube 62 having a check valve 64 therein is connected between the bottom of the container 14 and an inlet opening formed in the bottom of the pump chamber 22 and an outlet tube 66 is connected between an outlet opening formed in the top of the pump chamber 22 and one end of a hollow handle portion 68, the opposed end of which has the hypodermic needle nozzle 18 extending therefrom.

With the variable arrangement shown, adjustment of the stop member 44 accordingly adjusts the angular stroke of the cam follower arm 34, and thus also the stroke of the diaphragm 24. The period of time during which the cam 38 contacts the lever art 34 corresponds to the pulse of FIGS. 7 and 8, and the period when the cam 38 is not contacting the arm 34 corresponds to the relaxation period of FIGS. 7 and 8.

Another feature of this assembly is that the pump is preferably equipped with one check value 64 only on the inlet line. Nevertheless, check valves on both the inlet and the outlet may be used. Another feature of the present arrangement is that the forcing stroke is caused by the motor driven eccentric, whereas the springs cause the suction stroke. An eccentric or cam principle may be used instead of such springs, and the pump may be driven by a pair of cams-eccentrics, one serving for the driving stroke and the other for the suction stroke, but both being engaged part of the revolution only, making the stroke sharp and allowing the pump to be motionless for part of the revolution. One revolution in any case must represent then one full cycle.

Figure 15:
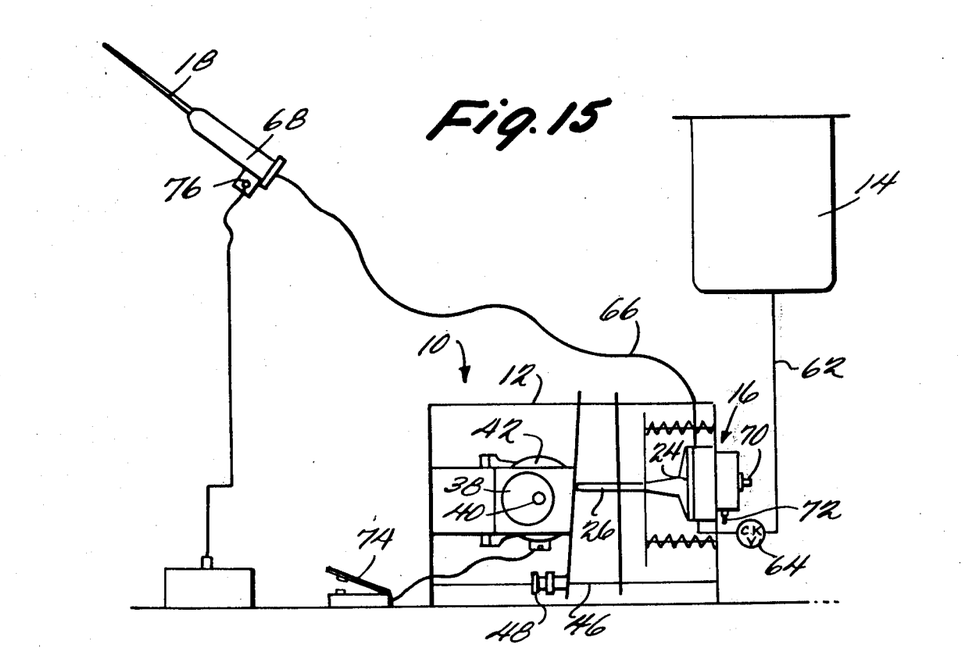
FIG. 15 is a schematic diagram of a complete assembly of apparatus for generating and applying the improved pulsed liquid jet stream of the present invention.

A complete apparatus for the production and application of a pulsed liquid jet stream, in accordance with the invention, is shown in FIG. 15. It consists of the device 10, as previously described, with an electric heater element 70 and thermostatic control 72 embedded in the pump body 20, to maintain body temperature in the liquid. The motor 42 is controlled by an on and off foot switch 74. The foot switch 74 may be combined with an rpm regulator, if desired. The valves used are preferably ball valves. The flexible tube or hose may conveniently be of 3/16 –¼ inches inside diameter and preferably spring coil reinforced in order to avoid absorbing of the pulsation. The elasticity of the hose can cause some absorption, and therefore the pulsation stream is inclined to be of the shape as in FIG. 8. Stroke frequency, pump capacity and nozzle opening are desirably in balance. Too high a frequency and/or capacity for too small a nozzle opening may cause undesirable changes in the shape of a pulsed stream — see FIGS. 16 and 17. The undesirable dental caries materials differ in mechanical properties from case to case and the following ranges were found practical:

1. Nozzle diameter — hypodermic needles gauge 33 to 10.
2. Frequency 100 – 1600 cycles/min., e.g., 250 –650 cycles per minute as noted in Example 2 infra.
3. Motionless period of the pump 50–95% during one cycle.
4. Flow rates 15 to 200 ml per minute.
5. Pressures 10 to 400 psi at the peak.

Figure 16:
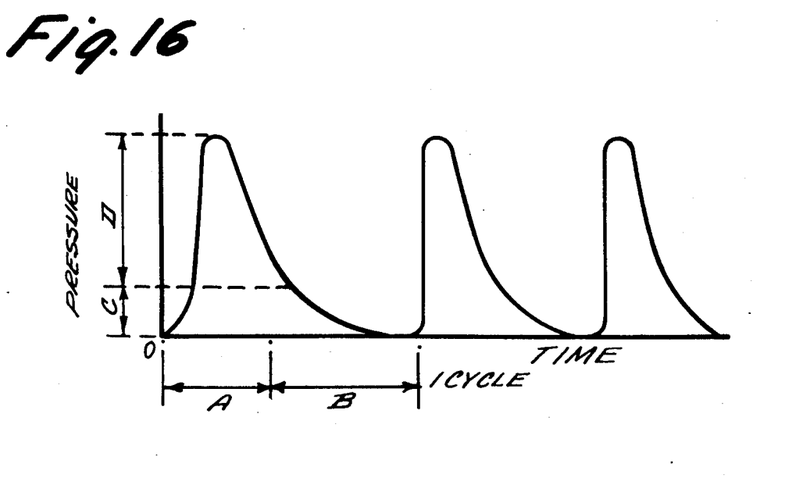
FIGS. 16 and 17 are graphs to show time-pressure relationships of an undesirable nature arising from too high a frequency and/or too low a capacity of nozzle opening.
Figure 17:
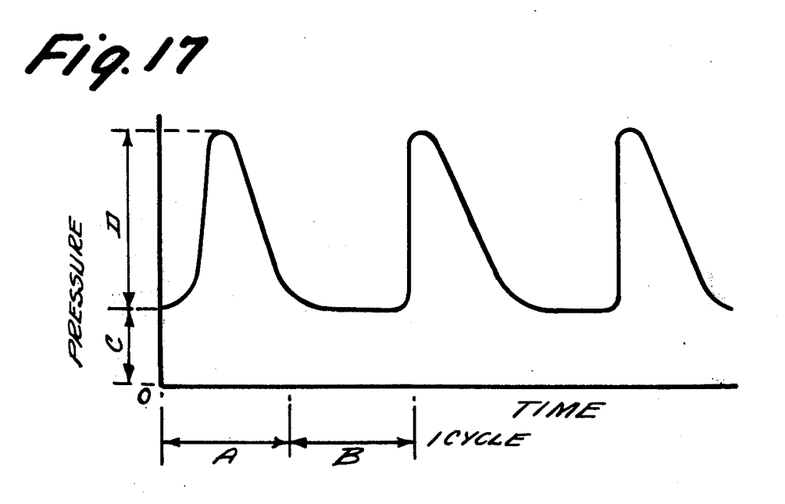

It was also found that a jet stream shown in FIG. 16 or 17 is applicable on harder materials if according to:
a. FIG. 16: A ≤ B (maximal A=50%) for C ≤ ⅓D (Maximal C=33% of D)
b. FIG. 17: A ≤ B and C ≤ ⅓D It was also found practical to use water, or water solution of different pH, preferably at body temperatures, for treatment.

EXAMPLE 1

Teeth cleaning — plaque removal

| Time | Frequency | Motionless Period | Nozzle | Peak Pressure | Flowrate | Liquid Medium |
|---|---|---|---|---|---|---|
| 15 min. | 400 | 85% | 21 gauge | 115 psi | 80 ml/min | Water |
| 12 min. | 150 | 50% | 15 gauge | 65 psi | 120 ml/min | Water |
| 10 min. | 650 | 90% | 21 gauge | 120 psi | 60 ml/min | Water |
| 14 min. | 1200 | 95% | 33 gauge | 300 psi | 75 ml/min | Water |
| 11 min. | 1600 | 95% | 20 gauge | 160 psi | 200 ml/min | Water |
| 12 min. | 600 | 92% | 20 gauge | 110 psi | 55 ml/min | Solution A |
| 12 min. | 650 | 90% | 21 gauge | 115 psi | 55 ml/min | Solution B |
| 8 min. | 550 | 75% | 14 gauge | 50 psi | 35 ml/min | Solution B |

Solution A
| | |
|---|---|
| NaOH | 0.05 moles/liter |
| NaCl | 0.05 moles/liter |
| Glycine | 0.05 moles/liter |
| Water as a solvent | |
| Resulting pH | 11.1 |

Solution B
As above with addition of 0.008 moles of NaClO per liter
Resulting pH  11.4

EXAMPLE 2

A decayed tooth prepared for filling

| Time | Frequency | Motionless Period | Nozzle | Peak Pressure | Flowrate | Liquid Medium |
|---|---|---|---|---|---|---|
| 5.5 min | 250 | 80% | 20 | 120 psi | 65 | Solution B |
| 4 min | 650 | 90% | 21 | 90 | 47 | Solution B |
| 12 min | 150 | 50% | 109 | 60 | 40 | Solution B |
| 11 min | 800 | 95% | 21 | 95 | 48 | Solution B |
| 14 min | 1200 | 95% | 20 | 135 | 57 | Solution B |
| 2.5 min | 500 | 85% | 20 | 85 | 30 | Solution B |

EXAMPLE 2-continued

A decayed tooth prepared for filling

| Time | Frequency | Motionless Period | Nozzle | Peak Pressure | Flowrate | Liquid Medium |
|------|-----------|-------------------|--------|---------------|----------|---------------|
| 7 min | 500 | 90% | 23 | 90 | 25 | Solution B |
| 8.5 min | 350 | 50% | 18 | 70 | 35 | Solution B |

While effective results are obtained with the apparatus as thus far described and exemplified above, these results were enhanced by further including in the apparatus, as shown in FIG. 15, a transducer 76 mounted on the handle 68 and electrically connected to an oscillator 78 for producing a desired ultra-sonic frequency.

The liquid jet is aimed to the tooth through the nozzle 18. The nozzle may be a tapered metal cylinder with a knurled surface for controlling the pulses. Disposable hypodermic needles may be used in the nozzle. The use of a needle as an orifice is desirable since it allows the pulse to be aimed at hard-to-reach areas in the mount and the dentist can scrape at the caries or plaque as the liquid jet is applied. Since the nozzle may often become clogged with plaque or other material it should be easy to exchange nozzles.

In a practical embodiment for dental plaque and caries removal, the following operating conditions were used:

1. pressure — between 10 and 400 psig.
2. Liquid flow rate — 20–150 ml. per minute.
3. Nozzle diameter — 15 to 30 gauge hypodermic needles used.
4. Operating temperature — 35° to 45° C preferably body temperature.
5. Pulse frequency — 100 to 1600 pulses per minute.
6. Dwell — 50 –90% of the cycle.

For the ultra-sonic generator attached to the nozzle, the frequency used is preferably between 5 – 75 KHz, preferably 20–25 KHz, and the energy output 5 to 50 watts. Ultrasonic vibrations increase the efficiency of the liquid jet and also improve the mechanical action of the nozzle. In operation, the nozzle may be used to scratch out the loose particles, and the ultra-sonic vibrations are found to make this operation very efficient.

According to the invention disclosed in my copending application Ser. No. 301,142, filed Oct. 26, 1972 and now U.S. Pat. 3,776,825, entitled "Electrolytic Treatment", the entire disclosure of which is hereby incorporated by reference, a solution of an alkali metal or an alkaline earth metal halide is decomposed electrolytically so as to provide free halogen which then reacts to form hypohalite in the presence of hydroxide ion. In order to form an N-halo derivative, the starting solution should also contain a suitable amino compound or compounds. The hypohalite reacts to form an N-halo derivative as soon as it is formed in the solution.

The starting solution may contain one or more alkali metal or alkaline earth metal halides.

Examples of suitable starting halides are sodium chloride, sodium bromide, sodium iodide, lithium chloride, lithium bromide, lithium iodide, potassium chloride, potassium bromide, potassium iodide, rubidium or cesium chloride, calcium chloride, calcium bromide, calcium iodide, strontium chloride, strontium bromide, strontium iodide, barium chloride, barium bromide and barium iodide.

The solution formed should have an alkaline pH usually 8 to 12 and preferably 10.5 to 11.5, most preferably 11 to 11.5. Desirably the electrolysis is carried out to form a solution 0.004 to 0.016 molar in N-haloamine. While not essential it is preferable to have present excess unhalogenated amine, i.e., in an amount up to 15 times the halogenated amine and preferably 6 to 8 times the N-halogenated amine on a molar basis.

As the amino nitrogen compounds there can be used either inorganic compounds such as sulfamic acid or organic compounds containing 2 to 11 carbon atoms, e.g., glycine, sarcosine, alpha-aminoisobutyric acid, taurine, 2-aminoethanol, N-acetylglycine, alanine, beta-alanine, serine, phenyl alanine, norvaline, leucine, isoleucine, proline, hydroxyproline, omega aminoundecanoic acid, glycylglycine, glycylglycylglycine, (and other polypeptides) aspartic acid, glutamic acid, glutamine, asparagine, valine, tyrosine, threonine, methionine, glutamine, tryptophane, histidine; arginine, lysine, alpha-aminobutyric acid, gamma-aminobutyric acid, alpha, epsilon diamino pimelic acid, ornithine, hydroxyl lysine, anthranilic acid, p-aminobenzoic acid, sulfanilic acid, orthanilic acid, phenyl sulfamic acid, aminopropanesulfonic acid, 2-aminoethanol, 2-aminopropanol, diethanolamine, ethylenediamine tetraacetic acid (EDTA),nitrilotriacetic acid and aminomethanesulfonic acid.

Examples of mono N-halo compound include N-chloroglycine, N-bromoglycine, N-iodoglycine, N-chlorosarcosine, N-bromosarcosine, N-iodosarcosine, N-chloro alpha amino isobutyric acid, N-chlorotaurine, N-bromotaurine, N-iodotaurine, N-chloro ethanolamine, N-chloro-N-acetyl-glycine, N-bromoethanol amine, N-iodoethanolamine, N-iodo-N-acetyl glycine, N-bromo-N-acetyl glycine, N-chloroalanine, glycine, N-chlorobeta alanine, N-bromo beta alanine, N-chloroserine, N-bromoserine, N-iodoserine, N-chloro-N-phenylalanine, N-chloroisoleucine, N-chloronorvaline, N-chloroleucine, N-bromoleucine, N-iodoleucine, N-chloroproline, N-bromoproline, N-iodoproline, N-chloro hydroxyproline, N-chloro omega aminoundeconoic acid, N-chloroaspartic acid, N-bromoaspartic acid, N-chloroglutamic acid, N-iodoglutamic acid, N-chlorovaline, N-chlorotyrosine, N-bromotyrosine, N-iodotyrosine, N-chlorothreonine, N-chloroglycylglycine, N-chloroglycylglycylglycine, N-chloromethionine, N-bromomethionine, N-chlorotryptophane, N-chlorohistidine, N-chloroargenine, N-chloroglutamine, N-bromoglutamine, N-chlorolysine, N-chloro gamma aminobutyric acid, N-chloro alpha, epsilon diaminopimelic acid, N-chloro ornithine, N-chloro hydroxylysine, N-chloroanthranilic acid, N-chloro p-aminobenzoic acid, N-chlorosulfamic acid, -N-chloro phenylsulfamic acid, N-chloro aminopropanesulfonic acid, N-aminomethanesulfonic acid, N-chloropropanolamine, N-chlorodiethanolamine, N-chloro ethylene diamine tetraacetic acid.

The solutions below may be prepared by the above-described electrolytic method to form the haloamines.

Solution (moles in a liter of a water solution)

| | NaCl | NaOH | Amino Compound |
|---|---|---|---|
| A | 0.10 | 0.08 | 0.05 glycine |
| B | KCl 0.15 | KOH 0.08 | 0.05 taurine |
| C | LiBr 0.15 | LiOH 0.08 | 0.05 glycine |
| D | NaI 0.10 | NaOH 0.12 | 0.10 sulfamic acid |
| E | CaCl$_2$ 0.10 | NaOH 0.07 | 0.05 glycine |
| F | NaCl 0.10 | NaOH 0.08 | 0.025 glycine 0.025 taurine |

As set forth in my copending application Ser. No. 301,163, filed Oct. 27, 1972, entitled "Dental Treatment", the entire disclosure of which is hereby incorporated by reference, the teeth are brought into contact with an N-haloamine also containing a hydroxy group, a sulfonic acid group, an N-acyl group, e.g., an N-acetyl group, or a carboxylic acid group. The halogen has an atomic weight of 35 to 127. Unless otherwise indicated in the present specification and claims the term "N-halo" means "N-monohalo".

Many of the N-halo compounds are unstable and they are conveniently prepared by reacting an alkali metal or alkaline earth metal hypohaline, preferably hypochlorite, with the amino compounds.

Examples of suitable hypohalites include sodium hypochlorite, potassium hypobromite, sodium hypoiodite, potassium hypoiodite, potassium hypobromite, rubidium hypochlorite, cesium hypochlorite, calcium hypobromite, strontium hypochlorite and barium hypochlorite.

For reacting with the hypohalite to form the N-halo compounds of the invention there can be used any of the aminocarboxylic acids or aminosulfonic acids previously set forth. The N-halo compounds formed and used in the present invention are those previously mentioned, e.g., N-chloroglycine. Solution B employed in example 1 and 2 is an illustration of forming N-monochloroglycine in situ from sodium hypochlorite and glycine.

Preferably there are employed N-halo amine carboxylic acids, e.g., aminoalkanoic acid free of divalent sulfur or free of a heterocyclic ring since when the divalent sulfur atom or the heterocyclic ring is present the N-halo compound has a very short half life.

The N-bromo and N-iodo compounds are the most effective but they have shorter half lifes than the N-chloro compounds and hence the N-chloro compounds are usually employed. Preferably the N-halo amino group is directly attached to an aliphatic carbon atom compounds which have an unpleasant odor preferably are not employed.

In Goldman et al. application Ser. No. 197,966 filed Nov. 11, 1971 now abandoned in favor of continuation-in-part application Ser. No. 307,835 filed Nov. 20, 1972, and now U.S. Pat. No. 3,886,266. there is disclosed the treatment of teeth to remove caries, dissolve plaque and prevent the development or buildup of calculus by the use of sodium, potassium or calcium hypochlorite a a pH of 9 to 11.5. Goldman et al. disclose there can be used non-toxic buffering agents and states that a preferred buffering agent is a mixture of glycine, sodium chloride and sodium hydroxide and specifically shows a mixture of an 0.5% solution of sodium hypochlorite, 1% glycine hydrochloride and sufficient sodium hydroxide to bring the pH to about 10°. They also disclose adding a mixture of 1 ml of flavor, 98 ml of a buffer solution 0.05 molar in glycine, 0.05 molar in sodium hydroxide and 0.05 molar in sodium chloride and 1 ml of 5% NaOCl to 500 ml of water and making the product up to 1000 ml with water. While Goldman et al. did not realize it they were making N-chloroglycine in situ by this procedure and it was the N-chloro-glycine which was the active agent in their process. Goldman et al. also disclose the use of a jet of the solution, e.g., from a mechanical pumping mechanism such as a WATER PIC $^{TM}$.

The parent nitrogen containing compound is preferably used in excess in forming the N-halo compound in situ from a hypohalite, e.g., the molar ratio of the parent nitrogen containing compound to available X$^+$ (from the hypohalite) should be 1:1 or greater, and preferably in the range of 2:1 to 15:1, most preferably 7:1. A mixture of nitrogen containing compounds can be used.

The available active X$^+$ concentration should preferably lie between 0.01% and 6%, and more preferably 0.05% and 1%.

The N-halo amino solutions should be used at a pH in the range of pH 8 to 12 and more preferably in the range of pH 10.5 to 11.5 inclusive, most preferably 11 to 11.5.

To maintain the preferred pH range it is desirable, because hydrogen ions are generated during the decomposition of an H-halo compound in aqueous solution to add a buffer system to the solution. Such buffer should be compatible with the N-halo compound, i.e., it should not have any deleterious effect thereon and it should be non-toxic. Borates and phosphates are examples of compatible salts for the formation of buffer systems, e.g., Na$_2$ H PO$_4$ can be used as the buffer since it can hold the pH above 10 even though in other systems it usually buffers at a lower pH.

Of course, mixtures of N-halo compounds can be employed.

Unless otherwise indicated all parts and percentages are by weight.

Formulations A – F below illustrate forming in situ N-haloamines which are illustrative of those which are effective in the present invention.

| Solution used | (Date are given in moles per liter of the water solution.) | | | | | |
|---|---|---|---|---|---|---|
| | NaOOl | NaOH | NaCl | Amino Compound | Buffer Salt | pH* |
| A | 0.008 | 0.0539 | 0.050 | 0.05 glycine | Na$_2$HPO$_4$ 0.0025 | 11.59 |
| B | 0.008 | 0.0640 | 0.050 | 0.05 glycine | Na$_2$B$_4$O$_7$ 0.00125 | 10.77 |
| C | 0.008 | 0.0210 | 0.050 | 0.05 glycine | Na$_2$B$_4$O$_7$ | 9.65 |

-continued

| Solution used | \multicolumn{5}{l}{(Data are given in moles per liter of the water solution.)} | |
|---|---|---|---|---|---|---|
| | NaOOl | NaOH | NaCl | Amino Compound | Buffer Salt | pH* |
| D | 0.008 | 0.0537 | 0.050 | 0.05 sulfamic acid | 0.00125 None | 11.49 |
| E | 0.008 | 0.0520 | 0.050 | 0.05 sulfamic acid | None None | 10.75 |
| F | 0.008 | 0.0548 | 0.050 | 0.05 taurine | None None None | 11.86 |

*The pH value of all solutions tested remained constant within 0.2 pH units for at least one hour.

Less preferably there can be used in the present invention N-dihaloamino compounds such as N-dichloroglycine, N-dibromoglycine, N-diiodoglycine, N-dichlorosarcosine, N-dibromosarcosine, N-diiodosarcosine, N-dichloro alpha amino isobutyric acid, N-dichlorotaruine, N-dibromotaurine, N-diiodotaurine, N-dichloroethanol-amine, N-diiodoethanolamine, N-dibromo beta alanine, N-dichloro beta alanine, N-dichloroalanine, N-dichlorserine, N-dibromoserine, N-diiodoserine, N-dichloroisoleucine, N-dichloronorvaline, N-dichloroleucine, N-dibromoleucine, N-diiodoleucine, N-dichloroproline, N-dibromoproline, N-diiodoproline, N-dichlorohydroxyproline, N-dichloro omega aminoundecanoic acid, N-dichloroaspartic acid, N-dibromoaspartic acid, N-dichloroglutamic acid, N-diiodoglutamic acid, N-dichlorovaline, N-dichlorotyrosine, N-dibromotyrosine, N-diiodotyrosine, N-dichlorothreonine, N-dichlorglycylglycine, N-dichloroglycylglycylglycine, N-dichloromethionine, N-dibromomethionine, N-dichlorohistidine, N-dichloroargenine, N-dichloroglutamine, N-ditromoglutamine, N-dichlorolysine, N-dichloro gamma aminobutric acid, N-dichloro ornithine, N-dichloro hydroxylylsine, N-dichloro p-aminobenzoic acid, N-dichloro sulfamic acid, N-dichloro aminopropanesulfonic acid, N-dichloroaminomethane sulfonic acid.

It thus will be seen that the objects of this invention have been fully and effectively accomplished. It will be realized, however, that the foregoing preferred specific embodiment has been shown and described for the purpose of illustrating the functional and structural principles of this invention and is subject to change without departure from such principles. Therefore, this invention includes all modifications encompassed within the spirit and scope of the following claims.

What is claimed is:

1. The method of removal of dental debris including plaque or caries which includes supplying liquid to a chamber having a movable wall whereby the size of the chamber can be changed, forcing the liquid out the chamber as a pulsating high velocity jet stream and applying said stream to the plaque or caries of a tooth, causing said pulsations by changing the size of the chamber by cyclically first rapidly increasing the pressure on the movable wall to reduce the size of the chamber, then at the same rate and for the same period of time decreasing the pressure on the movable wall to again change the size of the chamber and then employing a motionless period in the cycle of no change in pressure wherein the volume of the chamber remains constant, said pulsations being such that in each cycle the difference between the highest and lowest pressure applied to the dental debris, and the respective periods for which the dental debris in under highest pressure and lowest pressure cause the dental debris to be mechanically stressed and then completely relaxed during a motionless period of substantially nil application of pressure to the teeth.

2. The method of claim 1 wherein the motionless period is between 30 to 90% of the total period of each cycle.

3. The method of claim 1 wherein the dental debris comprises plaque.

4. The method of claim 1 wherein the dental debris comprises caries.

5. The method of claim 1 including the step of imparting ultra-sonic vibration to the jet stream prior to application thereof to the teeth.

6. The method of claim 1 wherein the liquid is an alkaline solution of N-haloamine selected from the group consisting of N-monohaloamines and N,N-dihaloamines containing a hydroxyl group, a sulfonic acid group, a carboxylic acid group or an N-acyl group.

7. The method of claim 6 wherein the dental debris comprises plaque.

8. The method of claim 6 wherein the dentaldebris comprises caries.

9. The method of claim 6 wherein the jet stream has a frequency of the order of 100 to 1600 cycles per minute and the period of nil pressure during each cycle is of the order of between 30 to 90% of the total period of each cycle.

10. The method of claim 9 wherein the jet stream has a frequency of the order of 250 to 650 cycles per minute.

11. The method of claim 10 wherein the dental debris includes caries.

* * * * *